Figure 1:
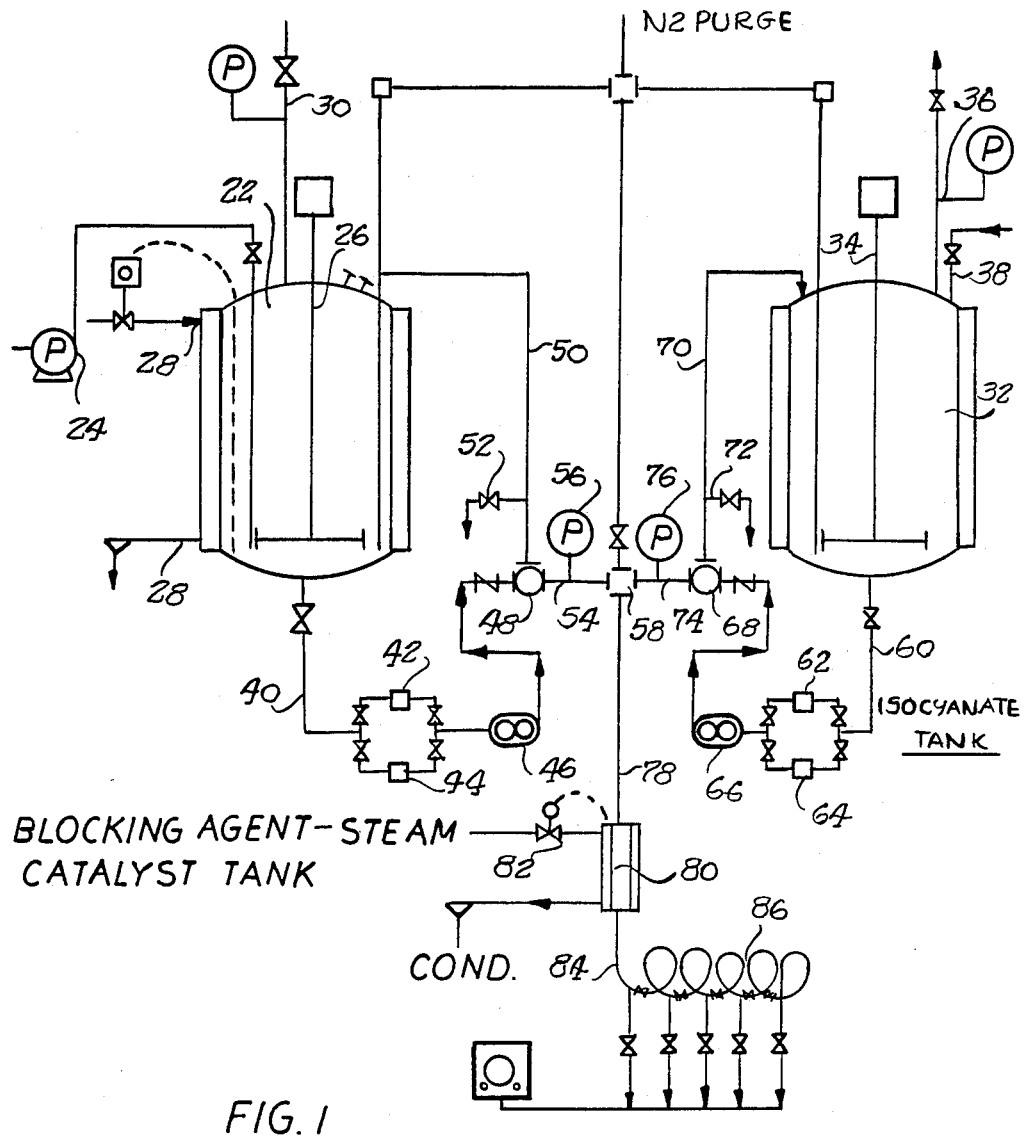

United States Patent [19]

Brinkman

[11] Patent Number: 4,868,298

[45] Date of Patent: Sep. 19, 1989

[54] CONTINUOUS PROCESS FOR THE PRODUCTION OF BLOCKED ISOCYANATE CONTAINING POLYISOCYANURATES

[75] Inventor: Larry F. Brinkman, Maple Grove, Minn.

[73] Assignee: Cargill, Incorporated, Minneapolis, Minn.

[21] Appl. No.: 209,837

[22] Filed: Jun. 22, 1988

[51] Int. Cl.$^4$ .................. C07D 401/14; C07D 403/14
[52] U.S. Cl. ..................................... 540/525; 540/202; 540/460; 540/524; 540/531; 544/193; 544/221; 544/222
[58] Field of Search ............... 540/202, 460, 524, 525, 540/531; 544/193, 221, 222

[56] References Cited

U.S. PATENT DOCUMENTS 4,306,051 12/1981 Gras et al. ........................ 544/193
4,696,491 12/1987 Kobayashi et al. ................. 544/193

Primary Examiner—Robert T. Bond
Attorney, Agent, or Firm—Fitch, Even, Tabin & Flannery

[57] ABSTRACT

A continuous method for the high-yield, one-step, solvent-free manufacture of blocked polyisocyanurate compounds useful as curing agents in powder coating compositions. The preferred method of manufacture is to pre-mix a blocking agent and a polymerization catalyst (BAC mix) prior to injection with an organic isocyanate monomer having two or more isocyanate groups (herein termed a polyisocyanate) into a preheated reaction zone wherein the BAC mix and the polyisocyanate react to form the blocked polyisocyanurate compound that is obtained after discharge from the reaction zone and cooling.

13 Claims, 1 Drawing Sheet

CONTINUOUS PROCESS FOR THE PRODUCTION OF BLOCKED ISOCYANATE CONTAINING POLYISOCYANURATES

BACKGROUND OF THE INVENTION

1. Field of the Invention

This invention relates to a continuous, one-step, solvent-free process for the high yield manufacture of polyisocyanurate compounds containing blocked, pendant isocyanate groups. This invention also relates to the compounds which may be obtained according to the process and to the use of these compounds as curing agents, in particular as curing agents in powder coating compositions.

As used herein, the terms polyisocyanate, polyisocyanurate and solvent-free process are defined as follows:

(a) Polyisocyanate. Polyisocyanate means any monomeric species containing two or more isocyanate groups bound to an alkyl, cycloalkyl or aromatic moiety.

(b) Polyisocvanurate. Polyisocyanurate means any polyisocyanate which has been cyclo-polymerized to form a single

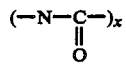

ring system ($x=2$, 3 or 4) which contains two or more pendant isocyanate groups; in particular, a polyisocyanate that has been polymerized to form the trimeric ring system

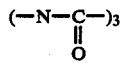

containing two or more pendant isocyanate groups.

(c) Solvent-free Process. Solvent-free process refers to a process or method of manufacture in which the polyisocyanate and the blocking agent are used in stoichiometric amounts, where the reaction has been carried out to substantial completion, and where no non-reactive inorganic or organic medium has been employed during the reaction.

2. Description of the Prior Art

Powder coating compositions and techniques have conventionally been used in the provision of protective films, and powder coating technology is becoming increasingly important for both economic and environmental reasons. Powder coating technology includes fluidized bed sintering techniques (such as electrostatic fluidized bed coating) and spray coating methods (such as electrostatic powder coating) which may be used or adapted for use with the various types of powder coating compositions. The compositions themselves may desirably be adapted and formulated to be, initially, sufficiently fluid to be capable of forming a film on the substrate under the coating conditions. The film may be subsequently curable by further polymerization and/or crosslinking.

There are a number of processes for the production of polyisocyanurates, the most important being the process in which a six member

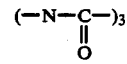

ring having pendant unreacted —R—NCO functional groups is produced by cyclo-trimerizing a polyisocyanate monomer, such as toluene diisocynate or isophorone diisocynate. A catalyst, selected for its ability to promote trimerization, is employed in these processes. When the desired polyisocyanurate is intended for use as a curing agent, a blocking agent may be added to the reaction mixture. The blocking agent reacts with the pendant isocyanate groups in a temperature reversible reaction to give a stable blocked polyisocyanurate product that can be used in powder coating formulations. The known processes, however, suffer from the drawback that either a non-reactive solvent must be used in the manufacturing process or that the reaction is run to completion so that the reactants can provide their own solvent. In either instance, costly and time consuming separation steps, such as filtration and drying, are required to isolate the blocked partial polyisocyanurate product. For example, U.S. Pat. No. 4,552,946 to Scholl et al states that when monomeric [poly] isocyanates are trimerized in the presence of a solvent, the reaction may be carried to the range of 50–70% completion. When the reaction is conducted without a solvent [non-reactive species], it is usually terminated after 10–25% completion; at which point reacted starting material is removed, usually in a thin film evaporator. Scholl et al, in effect, is using the polyisocyanate as a solvent. U.S. Pat. No. 4,454,317, to Disteldorf et al, in teaching trimerization of polyisocynates to polyisocyanurates, states a maximum conversion of 45% of starting material when the polyisocyanate is trimerized without a solvent. U.S. Pat. No. 3,919,218 to Schmitt et al, in teaching trimerization in the presence or absence of organic solvent, specifically teaches that the polyisocyanate itself can be used as a solvent. When the polyisocyanate is so used, the reaction is presumably stopped far short of completion because thin film separation of the starting material is specifically recommended by Schmitt et al.

In contrast to Scholl, Disteldorf and Schmitt, the present invention contemplates substantially complete conversion of the polyisocyanate reactant to a polyisocyanurate product. Further, unlike the references described above, the present invention does not require the product to be treated to remove the polymerization catalyst.

The production of blocked polyisocyanurates is taught by Gras et al in U.S. Pat. No. 3,313,876. In Gras et al, however, the production of the blocked polyisocyanurate is a multiple step process involving 50–80% starting material, polymerization, destruction and removal of the catalyst, and finally addition of the blocking agent. In contrast, according to the present invention the conversion from polyisocyanate to polyisocyanurate is substantially complete, no catalyst destruction or removal is required, and the blocking of the pendant isocyanate groups does not require a separate step.

A one-step synthesis of compounds containing blocked isocyanate groups has been taught by Panandiker et al in U.S. Pat. No. 4,055,551. However, Panandiker et al teaches the synthesis of blocked isocyanatopolyurethane (urethane: —C—O—C—N—C—) from a polyhydric alcohol, a diisocyanate and a blocking agent. In Panandiker et al, one of two isocyanate groups is reacted with an alcohol hydroxyl to form the urethane function and the other isocyanate group is blocked. Panandiker et al do not teach, nor can it be inferred, that in the absence of the polyhydric alcohol the diisocyanate would cyclo-trimerize to form the polyisocyanurate having a cyclic

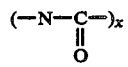

ring structure and pendant organoisocyanate groups. Contrarily, the prior art teaches that in the absence of any non-reactive solvent, complete polymerization should be avoided in order to prevent the formation of macromolecular multiple ring compounds.

Accordingly, there is a need for an improved method for manufacturing blocked polyisocyanurate compounds, and it is the object of this invention to provide such a method.

SUMMARY OF THE INVENTION

The present invention is a one-step method for manufacturing blocked cyclic polyisocyanurates comprising separately and continuously metering a catalyst, and stoichiometric proportions of a polyisocyanate monomer and a blocking agent into a reaction zone to provide a reaction mixture in the reaction zone at reaction temperature; providing a means for mixing the catalyst, polyisocyanate monomer and blocking agent in the reaction zone; maintaining the reaction mixture in the reaction zone for sufficient time at a sufficient temperature such that substantially all of the polyisocyanate monomer is cyclized and free isocyanate functionality of the reaction product indicates substantial completion of the reaction of the free isocyanate groups with the blocking agent to form a blocked polyisocyanurate; and continuously withdrawing the blocked polyisocyanurate reaction product from the reaction zone after the cyclization and blocking reactions are substantially completed. This invention is particularly applicable to the trimerization of polyisocyanates so as to form a six-members

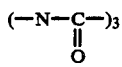

ring system in which pendant organoisocyanate groups are attached to the ring nitrogen via the organic moiety, and the free isocyanate function of the organoisocyanate is blocked by an appropriate blocking agent to thereby form a blocked polyisocyanurate.

In the process of producing blocked polyisocyanurates by the method of this invention, either three separate streams of reactants, viz. catalyst, polyisocyanate and blocking agent, may be separately metered into the reactor and the three components mixed therein; or, in the preferred embodiment, the catalyst can be mixed with the blocking agent and the combination metered into the reactor via a single line. This premixing of the catalyst and the blocking agent has the advantage of reducing equipment costs and minimizing the number of reactor input streams the operators have to monitor. In addition, combining the catalyst and blocking agent streams serves to dilute the catalyst and thus avoids a high, localized polyisocyanate-catalyst concentration within the reaction zone when the catalyst is contacted with the polyisocyanate. A high catalyst-polyisocyanate concentration could lead to a runaway reaction.

In the process, according to the present invention, the polyisocyanates useful for polymerization to a cylic, trimeric polyisocyanurate may be used either singly or as a component of a mixture of polyisocyanates. The polyisocyanates utilizable in this invention are a well known class of materials and may include aromatic, aliphatic and cycloaliphatic isocyanates. A partial list of the aromatic isocyanates which may be utilized in this invention includes 2,4- or 2,6-toluene diisocyanate; 2,4-diphenylmethane diisocyanate; tris (4-isocyanatophenyl) methane; 1,5-napthalene diisocyanate; and 2,4,6-triisocyanatotoluene. A partial list of the aliphatic and cycloaliphatic polyisocyanates which may be utilized in this invention includes isophorone diisocyanate (3-isocyanate-3,5,5-trimethyl-5-isocyanatomethylcyclohexane); hexamethylene diisocyanate; 1,3- or 1,4-cyclohexane diisocyanate; 1-methyl-(2,4- or 2,6-)diisocyanatocyclohexane; 1,3-cyclobutane diisocyanate; dodecamethylene diisocyanate and tetramethylene diisocyanate.

Suitable blocking groups for the free or pendant isocyanate groups that remain after the polyisocyanates have been cyclized to polyisocyanurates may be selected from materials consisting of lactams and ketoximes. Particularly suitable blocking groups are epsilon caprolactam, delta valerolactam, and methyl ethyl ketoxime.

Prior art catalysts, such as those described in the above cited references, that are known to be efficient polyisocyanate cyclotrimerization catalysts are included as polymerization catalysts of this invention. The preferred catalysts among this group, because of their ability to effect substantially complete conversion of the polyisocyanate starting material to a cyclotrimerized polyisocyanurate, are complex metal hydrides and salts of alkoxymetal hydrides such as sodium borohydride, lithium aluminum hydride, potassium tris(isopropoxy)boron hydride, sodium bis (2-methoxyethoxy)aluminum hydride, lithium tris(isopropoxy)boronhydride, and lithium tris(t-butoxy)aluminum hydride. These catalysts may be used separately or in combination in the method of this invention.

FIG. 1 of the drawing discloses apparatus schematically for the practice of the invention.

EXAMPLES

The present invention will now be more particularly described with reference to FIG. 1, which depicts apparatus adapted to carry out a preferred embodiment of the present invention.

While this invention can be carried out using separate catalyst, blocking agent and polyisocyanate reactant input streams, in the preferred embodiment as illustrated in FIG. 1, the blocking agent is melted (if a solid) and mixed with the catalyst in an off-line tank (not shown). The blocking agent-catalyst (BAC) mixture is then transferred to the on-line BAC tank 22 by means of pump 24. The BAC mixture is provided with mixing 26, steam service 28 and vent 30 means. A polyisocyanate on-line tank 32 is also equipped with suitable mixing 34, venting 36, and filling 38 means. The on-line tanks 22 and 32 serve as reservoirs for the reaction process.

The BAC tank 22 is provided with a metering conduit 40 including suitable filters 42, 44 and a metering pump 46. The metering pump 46 directs the BAC mixture to a three-way valve 48, one outlet of which is directed to a recycle line 50 which returns to the BAC tank 22. The recycle line 50 includes manual calibration apparatus 52 which may be used to calibrate the flow controlled by the metering pump 46 when the three-way valve 48 is directed so that the recycle line 50 is the only outlet. The other outlet of the three-way valve 48 is the process outlet line 54 which includes an appropriate measuring gauge 56. The process outlet line 54 serves as an input feed to a three-way valve 58.

Similarly, the polyisocyanate tank 32 is provided with a polyisocyanate metering conduit 60 including appropriate filters 62, 64 and metering pump 66. The polyisocyanate metering pump 66 similarly feeds into a three-way valve 68 which has as one outlet a recycle line 70 which is directed back into the polyisocyanate tank 32. The polyisocyanate recycle line 20 is also provided with appropriate manual calibration apparatus 72. The other outlet of the three-way isocyanate valve 68 is the polyisocyanate process outlet line 74 which is similarly provided with appropriate pressure and other measuring apparatus 76. The process outlet line 74 from this isocyanate metering and delivery system serves as the other inlet to the three-way valve 58, the first inlet being the blocking agent-catalyst process outlet line 54, as described herein above.

Through appropriate adjustment of the respective metering pumps 46 and 66, the BAC mixture and the polyisocyanate may be metered in the desired stoichiometric ratio to the three-way valve 58 on a continuous and simultaneous basis to provide a reactant feed, in proper stoichiometric proportions, into the reactor feed line 78. The reactor feed line 78 discharges into reactor 80 which may be a dynamic mixer, or the reactor 80 may be equipped with a stirring device, to intimately mix the BAC and the polyisocyanate components. Though not required, the reactor feed line 78 can also be equipped with a static mixing device to pre-mix the BAC and polyisocyanate components prior to discharge into the reactor.

The reaction mixture is, concomitantly with the introduction of the feed materials into the mixing zone by means of a feed line 78, conducted from the reactor 80 and subsequently cooled and processed. The reaction zone 80 provides reaction residence time and any combination of static, dynamic or stirrer mixing device serves to provide appropriate mixing and time-temperature conditions in an overall continuous process system reaction zone.

The overall blocking agent-polyisocyanate reaction is exothermic and accordingly provides heat to the reaction. Using a procedure known to those acquainted with the art, the exothermic nature of the reaction is used to preheat the reactor 80 by filling the reactor with the BAC-polyisocyanate mixture, stopping feed flow from feed line 78 into the reactor, and allowing the feed mixture within the reactor to reach its maximum temperature. Once the maximum temperature has been reached, feed line 78 is opened and continuous processing is begun. By carefully regulating the feed rate to maintain approximately the maximum temperature, the BAC-polyisocyanate mixture will be maintained in the overall reaction zone for a sufficient length of time to provide for substantial completion of cyclotrimerization and the blocking agent-polyisocyanurate reactions. Substantial completion of the overall reaction is indicated by the presence of less than 2%, and preferably less than 1%, of free isocyanate groups, based on the number of isocyanate groups in the polyisocyanate monomer. Generally, the reactants will be maintained in the overall reaction zone for a period of time in the range of 5 to 300 seconds, and the volume of the reaction zone and the metering rate of the reactants will be adjusted to provide for an appropriate reaction zone retention time.

The reaction mixture should not be held at high reaction temperature under long residence time conditions as this is deleterious to the final product. For example, maintaining the mixture in the reaction zone at too high a temperature for too long a time could lead to the formation of a macromolecular product containing multiple cyanurate rings. In another example, maintaining methyl ethyl ketoxime blocked polyisocyanurates about a temperature of 280°-320° F. for more than 90 seconds results in the undesirable development of dark color in the final product.

The finished product may be directly discharged from the reaction zone 80 to a cooling belt 81 for final cooling and subsequent processing.

The following specific examples are given to illustrate the invention described herein.

EXAMPLE 1

A blocked polyisocyanurate product was prepared in the laboratory by melting 1.053 moles of epsilon caprolactam in a reaction vessel and adding 0.074 moles of the catalyst sodium bis(methoxyethoxy)aluminum hydride to form a BAC mixture. This mixture was heated to 190° F. Isophorone diisocyanate (1.000 mole) was added to the BAC mixture with stirring. The reaction mixture exothermed to 340° F. within 300 seconds. It was then poured into a tray to cool. The free isocyanate content of the blocked polyisocyanurate reaction product was less than 2%.

EXAMPLE 2

A reaction according to the procedure described in Example 1 was carried out using 0.028 moles of sodium borohydride dissolved in 0.116 moles of water as the catalyst. The free isocyanate content of the blocked polyisocyanurate reaction product was less than 2%.

EXAMPLE 3

A reaction according to the procedure described in Example 1 was carried out using 1,000 moles of toluene diisocyanate as the polyisocyanate monomer and 0.0005 mole of sodium bis(2-methoxyethoxy)aluminum hydride as the catalyst. The free isocyanate content of the blocked polyisocyanurate reaction product was less than 2%.

EXAMPLE 4

A blocked polyisocyanurate was prepared in a laboratory scale run by continuously and separately metering a BAC mixture as described in Example 1 and isophorone diisocyanate in stoichiometric amounts into the inlet side of a laboratory scale, continuous reaction apparatus substantially equivalent to that described above. The isophorone diisocyanate was heated to 100° F. before introduction into the reaction zone and the BAC mixture was heated to 190° F. before introduction into the reaction zone. The peak exotherm reached in the reaction was about 350° F. The exotherm collapses about 90 seconds after the two reactant streams were first contacted. Total residence time in the reaction zone prior to ejecting the product onto a cooling tray was about 220 seconds. The free isocyanate content of the blocked polyisocyanurate reaction product was less than 1%.

EXAMPLE 5

A reaction according to Example 4 was carried out using a BAC mixture as described in Example 2. The free isocyanate content of the blocked polyisocyanurate was less than 2%.

EXAMPLE 6

A reaction according to Example 4 was carried out using the reactants described in Example 3. The free isocyanate content of the blocked polyisocyanurate reaction product was less than 1%.

EXAMPLE 7

A blocked polyisocyanurate was prepared in a laboratory scale run by continuously and separately metering a BAC mixture of 1.062 moles of methyl ethyl ketoxime and 0.006 mole of sodium bis(2-methoxyethoxy)aluminum hydride and toluene diisocyanate in a molar ratio of polyisocyanate to ketoxime of 1.000 to 1.062 into the inlet side of a laboratory scale continuous reaction apparatus substantially equivalent to that described above. The toluene diisocyanate was heated to 120° F. before introduction to the reaction zone and the BAC mixture was held at room temperature before introduction into the reaction zone. The peak exotherm reached in the reaction zone was about 325° F. Total residence time in the reaction zone prior to ejecting the reaction product onto a cooling tray was about 100 seconds. The free isocyanate content of the blocked polyisocyanurate reaction product was less than 2%.

The various features of the invention which are believed to be new are set forth in the following claims.

What is claimed is:

1. A method for the one-step manufacturing of blocked cyclic polyisocyanurates comprising continuously metering a catalyst and stoichiometric proportions of a polyisocyanate monomer and a blocking agent into a reaction zone to provide a reaction mixture in the reaction zone at reaction temperature;

mixing the catalyst, polyisocyanate monomer and blocking agent in the reaction zone;

maintaining the reaction mixture in the reaction zone for sufficient time at a sufficient temperature such that substantially all of the polyisocyanate monomer is cyclized and free isocyanate functionality of the reaction product indicates substantial completion of the reaction of free isocyanate groups with the blocking agent to form a blocked polyisocyanurate; and continuously withdrawing the blocked polyisocyanurate reaction product from the reaction zone after the cyclization and blocking reactions are substantially completed.

2. A method in accordance with claim 1 wherein the cyclic polyisocyanurate is a trimmer and the free isocyanate functionality of the reaction product indicates substantial completion of the reaction of free isocyanate groups with the blocking agent to form a blocked polyisocyanurate.

3. A method in accordance with claim 2 wherein the blocking agent and the catalyst are first mixed together to form a mixture which is capable of being injected into the reaction zone.

4. A method in accordance with claims 2 or 3 wherein the polyisocyanate is selected from the group consisting of 2,4'- or 2,6-toluene diisocyanate; isophorone diisocyanate; 2,4'-diphenylmethane diisocyanate; tris(4-isocyanatophenyl) methane; 1,5-napthalene diisocyanate; 2,4,6-triisocyanatotoluene; hexamethylenediisocyanate; 1,3 or 1,4-diisocyanatocyclohexane; 1-methyl-(2,4- or 2,6-)diisocyanatocyclohexane and mixtures thereof.

5. A method in accordance with claim 2 or 3 wherein the blocking agent is selected from the group consisting of lactams and ketoximes.

6. A method is accordance with claim 5 wherein the blocking agent is selected from the group consisting of epsilon caprolactam, delta valerolactam, and methyl ethyl ketoxime.

7. A method in accordance with claim 2 or 3 wherein the catalyst is selected from the group consisting of complex metal hydrides and salts of alkoxymetal hydrides.

8. A method according to claim 7 wherein the catalyst is selected from the group consisting of lithium aluminum hydride, sodium borohydride, sodium bis(2-methoxyethoxy)aluminum hydride, lithium tris(isopropoxy)boron hydride and tris(t-butoxy)aluminum hydride.

9. A method in accordance with claim 2 or 3 wherein the reaction mixture is maintained in the reaction zone for a period of time in the range of about 15 to about 300 seconds.

10. A method in accordance with claim 2 or 3 wherein the reaction mixture is maintained in the reaction zone for a period of time sufficient to establish a free isocyanate level in the reaction product of less than 1%.

11. A method in accordance with claim 2 or 3 wherein the catalyst is employed to generate a peak reaction exotherm in the reaction zone.

12. A method in accordance with claim 2 or 3 wherein the reaction zone is maintained at a temperature in the range from about 250° to about 400° F.

13. A method in accordance with claim 2 or 3 wherein a reaction temperature above the unblocking temperature of the blocking agent, in respect to the polyisocyanate, is maintained in the reaction zone.

* * * * *

UNITED STATES PATENT AND TRADEMARK OFFICE
CERTIFICATE OF CORRECTION

PATENT NO. : 4,868,298

DATED : September 19, 1989

INVENTOR(S) : Larry F. Brinkman

It is certified that error appears in the above-identified patent and that said Letters Patent is hereby corrected as shown below:

Column 1, line 23, change "Polvisocvanurate" to

--polyisocyanurate--.

Column 3, line 43, change "six members" to --six-member--.

Column 4, line 20, change "2,6-)diisocyanatocyclohexane;"

to --2,6-) -diisocyanatocyclohexane;--.

Column 4, lines 41-42, change "(2-methoxyethox-y)-" to

--(2-methoxyethoxy)--.

Column 6, line 15, change "about" to --above--.

Column 6, line 20, after "zone 80", insert --through conduit 84--.

UNITED STATES PATENT AND TRADEMARK OFFICE
CERTIFICATE OF CORRECTION

PATENT NO. : 4,868,298
DATED : September 19, 1989
INVENTOR(S) : Larry F. Brinkman It is certified that error appears in the above-identified patent and that said Letters Patent is hereby corrected as shown below:

Column 6, line 20, change "cooling belt 81" to --cooling loop 86--.

Column 7, lines 22-23, change "(2-methoxyethox-y)" to --(2-methoxyethoxy)--.

Claim 3, column 8, line 9, change "claim 2" to --claim 1--.

Signed and Sealed this

Eighth Day of January, 1991

Attest:

HARRY F. MANBECK, JR.

Attesting Officer

Commissioner of Patents and Trademarks